US00PP08152P

United States Patent [19]

van der Knaap

[11] Patent Number: Plant 8,152

[45] Date of Patent: Feb. 16, 1993

[54] CHRYSANTHEMUM PLANT — LIERWAY CULTIVAR

[75] Inventor: Jacques C. M. van der Knaap, De Lier, Netherlands

[73] Assignee: Fides Beheer B.V., De Lier, Netherlands

[21] Appl. No.: 720,934

[22] Filed: Jun. 25, 1991

[51] Int. Cl.[5] ..... A01H 5/00

[52] U.S. Cl. ..... Plt./82.2

[58] Field of Search ..... Plt./74.1, 82.2

*Primary Examiner*—Howard J. Locker

*Attorney, Agent, or Firm*—Burns, Doane, Swecker & Mathis

[57] ABSTRACT

A new and distinct cultivar of Chrysanthemum plant named Lierway is provided. The new cultivar is a spontaneous mutation of the Broadway cultivar (U.S. Plant Pat. No. 6,737) and exhibits distinctively colored blossoms of the generally flat capitulum form and the single capitulum type. More specifically, the new cultivar forms attractive yellow flowers having an anthocyanin dot at the flower center which can be readily distinguished from the soft pink flowers of the Broadway parent which include a similar dark dot at the flower center. The new cultivar is particularly suited for use in the production of a cut daisy spray under greenhouse conditions.

1 Drawing Sheet

SUMMARY OF THE INVENTION

The present invention comprises a new and distinct cultivar of Chrysanthemum, botanically known as *Chrysanthemum morifolium.*, Ramat., and hereinafter is referred to by the cultivar name Lierway.

The new Lierway cultivar is a spontaneous mutation of unknown causation which was discovered and carefully preserved during the course of plant selection work which was conducted by me. The new cultivar was discovered during April, 1987 among plants of the Broadway cultivar (U.S. Plant Pat. No. 6,737) being grown under my direct supervision at De Lier, The Netherlands.

It was observed that a plant consistently formed distinctive yellow flowers having yellow ray florets which convey a different overall appearance than the soft pink ray florets of the Broadway cultivar. The new variety continues to exhibit a dark anthocyanin dot at the flower center which is very similar to that of the Broadway cultivar. All of the other characteristics of this plant were found to be substantially identical to those of the Broadway cultivar. Had I not discovered, carefully studied, and preserved this new cultivar, it would have been lost to mankind. This new cultivar is particularly well suited for growing in the production of a cut daisy spray.

It was found that the new cultivar of the present invention:

(a) exhibits attractive yellow flowers having an overall diameter of approximately 60 to 75 mm. wherein the ray florets are yellow and the flower center bears a distinctive anthocyanin dot,
(b) exhibits a flower response period of approximately nine weeks,
(c) forms attractive dark green foliage, and
(d) has the ability to produce flowers of commercially acceptable quality throughout the year in a cut mum production program.

Asexual reproduction of the new cultivar by cuttings as performed at De Lier, The Netherlands, in a controlled environment has demonstrated that the characteristics of the new cultivar as herein disclosed are firmly fixed and are retained through successive generations of asexual propagation.

Lierway has not been observed under all possible environmental conditions to date. Accordingly, it is possible that the phenotype may vary somewhat with variations in the environment, such as temperature, light, day length, contact with pesticides and/or subjection to growth retardant treatments.

The new cultivar of the present invention because of the distinctive ray floret coloration also can be readily distinguished from the Glamour cultivar (non-patented in the United States) which exhibits pink ray florets in combination with a dark dot at the flower center.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is The R.H.S. Colour Chart of The Royal Horticultural Society, London, England. The color values were determined at 11:00 a.m. to 12:00 noon under natural daylight conditions at De Lier, The Netherlands, during May, 1991. The plants described were grown under standard greenhouse conditions which approximate those commonly utilized for the production of cut mums.

Classification:

*Botanical.*—*Chrysanthemum morifulium* Ramat., cv. Lierway.

*Commercial.*—Cut daisy spray.

INFLORESCENCE

A. Capitulum:

*Form.*—When mature, flat to slightly cupped.

*Type.*—Single.

*Diameter across face.*—Approximately 60 to 75 mm. on average.

B. Corolla of ray and disc florets:

*Color (general tonality from a distance of three meters).*—Yellow with dark center.

*Color ray florets. (top surface).*—Yellow, Yellow-Orange Group 15A.

*Color disc florets.*—At the center there is an anthocyanin dot which is near Greyed-Orange Group 175A in coloration.

C. Reproductive organs:

*Androecium.*—Present in disc florets, numerous.

*Gynoecium.*—Present in both disc and ray florets, numerous.

PLANT

A. General appearance:

*Height.*—Approximately 85 cm. on average.

B. Foliage:

*Color (upper surface).*—Yellow-Green Group 147A.

*Color (under surface).*—Yellow-Green Group 147B.

I claim:

1. A new and distinct cultivar of Chrysanthemum plant named Lierway, substantially as herein shown and described, which:

(a) exhibits attractive yellow flowers having an overall diameter of approximately 60 to 75 mm. wherein the ray florets are yellow and the flower center bears a distinctive anthocyanin dot, (b) exhibits a flower response period of approximately nine weeks, (c) forms attractive dark green foliage, and (d) has the ability to produce flowers of commercially acceptable quality throughout the year in a cut mum production program.

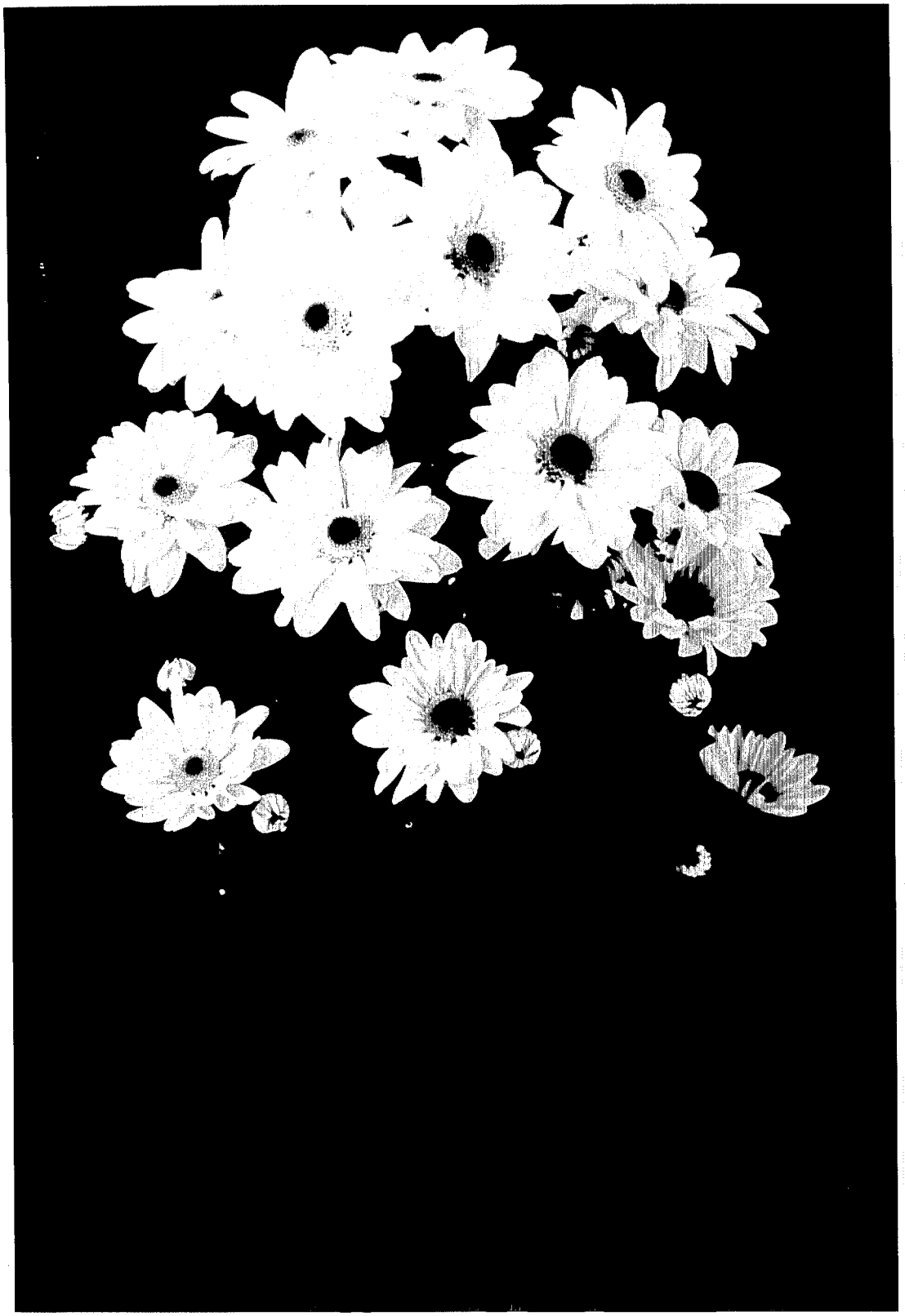

* * * * *